(12) United States Patent
Sanderson

(10) Patent No.: US 6,322,724 B1
(45) Date of Patent: Nov. 27, 2001

(54) PRODUCTS FOR CONTROLLING EVAPORATIVE MOISTURE LOSS AND METHODS OF MANUFACTURING THE SAME

(75) Inventor: George R. Sanderson, Carlsbad, CA (US)

(73) Assignee: ISP Investments Inc., Wilmington, DE (US)

(*) Notice: Subject to any disclaimer, the term of this patent is extended or adjusted under 35 U.S.C. 154(b) by 0 days.

(21) Appl. No.: 09/478,259

(22) Filed: Jan. 5, 2000

(51) Int. Cl.[7] .............................. C09K 3/00; C01B 31/16
(52) U.S. Cl. ............................. 252/194; 252/184
(58) Field of Search ...................... 252/194, 184

(56) References Cited

U.S. PATENT DOCUMENTS

| | | | |
|---|---|---|---|
| 4,659,560 | * 4/1987 | Bews et al. | 424/47 |
| 4,883,478 | * 11/1989 | Lerailler et al. | 604/360 |
| 4,983,390 | * 1/1991 | Levy | 424/404 |
| 5,079,354 | * 1/1992 | Gross et al. | 536/111 |
| 5,432,215 | * 7/1995 | Girg et al. | 524/28 |
| 5,472,761 | * 12/1995 | Goldberg et al. | 428/76 |
| 5,550,189 | * 8/1996 | Qin et al. | 529/54.3 |
| 5,989,446 | * 11/1999 | Hicks et al. | 252/8.05 |
| 6,107,432 | * 8/2000 | Engelhardt et al. | 529/311 |

* cited by examiner

Primary Examiner—Joseph D. Anthony
(74) Attorney, Agent, or Firm—Imre Balogh; William J. Davis; Walter Katz

(57) ABSTRACT

The present invention is directed towards compositions which contain a crosslinked absorbent polymer and a water soluble low molecular weight compound. The water soluble low molecular weight compound reduces the rate at which water evaporates from the crosslinked absorbent polymer. The crosslinked absorbent polymers of this invention have a water retention value greater than or equal to about 6. This invention also is directed towards methods for preparing the compositions of this invention.

25 Claims, 1 Drawing Sheet

PRODUCTS FOR CONTROLLING EVAPORATIVE MOISTURE LOSS AND METHODS OF MANUFACTURING THE SAME

BACKGROUND OF THE INVENTION

1. Field of the Invention

This invention relates to water absorbent compositions. This invention also relates to a process for preparing such compositions.

2. Discussion of the Related Art

Superabsorbents are hydrogels which are capable of absorbing many times their weight in water. Superabsorbent polymers, synthetic, part synthetic or hydrocolloid based, have been well known for over 30 years. Examples of synthetic superabsorbents are the crosslinked polyacrylamides and polyacrylic acids. Starch/polyacrylonitrile graft copolymers are part synthetic, while crosslinked carboxymethylcellulose and crosslinked carboxymethyl starches are examples of hydrocolloid superabsorbent polymers.

The use of superabsorbents has been contemplated in applications in which immobilization of water or aqueous fluids within a swollen, hydrogel network is required. For example, these polymers have been proposed as potentially useful in such products as diapers, sanitary napkins and the like, as well as protective coatings for seeds, controlled delivery vehicles for drugs, herbicides, pesticides and insulating materials. An extensive list of synthetic superabsorbents is given in U.S. Pat. No. 4,983,390, the entire contents of which are incorporated by reference herein.

In many regions of the world, and in particular in the more arid regions, there is a major need to conserve precious water resources and to maximize water's effectiveness in horticultural uses. Because of superabsorbents' high water absorption capacity and their ability to dry out and rehydrate many times in succession, they have been considered as potentially useful tools in the area of water conservation. However, synthetic and part synthetic superabsorbents suffer from the disadvantage that they are not biodegradable and sometimes contain residual and undesirable quantities of unreacted monomer. In addition, it has been reported that polyacrylamides, by themselves, do not reduce the rate at which water is lost by evaporation from soil. Letey. J. et al., Calif. Agric., May/June 1992, pp. 9–10; Tayel, M. Y. and El-Hady, O. A., Acta. Horticultrae, 119 (1981) pp. 247–256.

In contrast to synthetic and semi-synthetic superabsorbents, hydrocolloid based superabsorbents are readily degraded by bacteria, ultimately to carbon dioxide, water and other small molecules. For this reason, hydrocolloid based superabsorbents, such as the crosslinked carboxymethylated starch derivatives described in British Patent No. 1,576,475, are particularly attractive as candidates for helping conserve water resources.

However, the ability of a material to absorb large amounts of water does not necessarily guarantee that the material will be effective in water conservation uses. This is demonstrated by the example of polyacrylamides, which are superabsorbents, but which do not reduce the rate at which water is lost by evaporation from soil. Thus, polyacrylamides allow water to be added to soil less frequently, but not in lower amounts. The application of superabsorbents in water conservation depends upon their ability to reduce the rate at which water is lost from soil by evaporation.

Colligative properties, such as boiling point elevation and freezing point depression, depend upon the number of solute molecules in solution. Consequently, high molecular weight solutes are much less effective than low molecular weight solutes in influencing these properties. For example, 10 grams of a high molecular weight hydrocolloid is much less effective in elevating the boiling point of water than are 10 grams of sucrose because there are more molecules of sucrose in 10 grams of sucrose than there are molecules of hydrocolloid in 10 grams of hydrocolloid.

A superabsorbent composition having a reduced rate of water evaporation would be desirable. Such a composition could be added to soil to enhance water conservation.

Alginates are obtained from brown seaweed. They have been used in industry as food hydrocolloids for a long time. Structurally, alginates are linear polymers composed of mannuronic acid and guluronic acid. Functionally, alginates may be used as viscosifying or gelling agents in water-based systems. At low calcium ion concentrations, alginates function as viscosifying agents. At high calcium ion concentrations, alginates function as gelling agents.

Use of alginate as a thickener is relatively straightforward, provided that the polymer is properly hydrated and dispersed. Gel formation, normally induced at room temperature, may be brought about by controlled release of calcium ions into the system. A number of ways for obtaining this controlled release are well known by those skilled in the art. Many of these involve the use of sequestrants, typically sodium citrate, to compete with the alginate for the calcium as it is being released.

Alginates can also form gels and precipitates with acid. Propylene glycol alginates have enhanced acid stability. These alginates are often used as stabilizers in beverages, syrups, salad dressings and beer.

A by-product of manufacturing processes for alginate is alginate product which does not meet the specification requirements of the end use application. It would be highly desirable to provide a commercial use for such unusable alginate while simultaneously providing water absorbent products which reduce the rate of water evaporation from soil.

SUMMARY OF THE INVENTION

The present invention is directed towards absorbent compositions comprising a crosslinked absorbent polymer and a water soluble low molecular weight compound. The water-soluble low molecular weight compound reduces the rate at which water evaporates from the crosslinked absorbent polymer. The crosslinked absorbent polymers of this invention have a water retention value greater than or equal to about 6 grams of water per gram of polymer. The composition of this invention also may contain a low molecular weight carbohydrate polymer. The low molecular weight carbohydrate polymer may be used to replace a portion of the crosslinked absorbent polymer without significantly affecting the absorbent capacity of the composition. This invention also is directed towards methods for preparing the compositions of this invention.

DETAILED DESCRIPTION OF THE INVENTION

Figure 1:
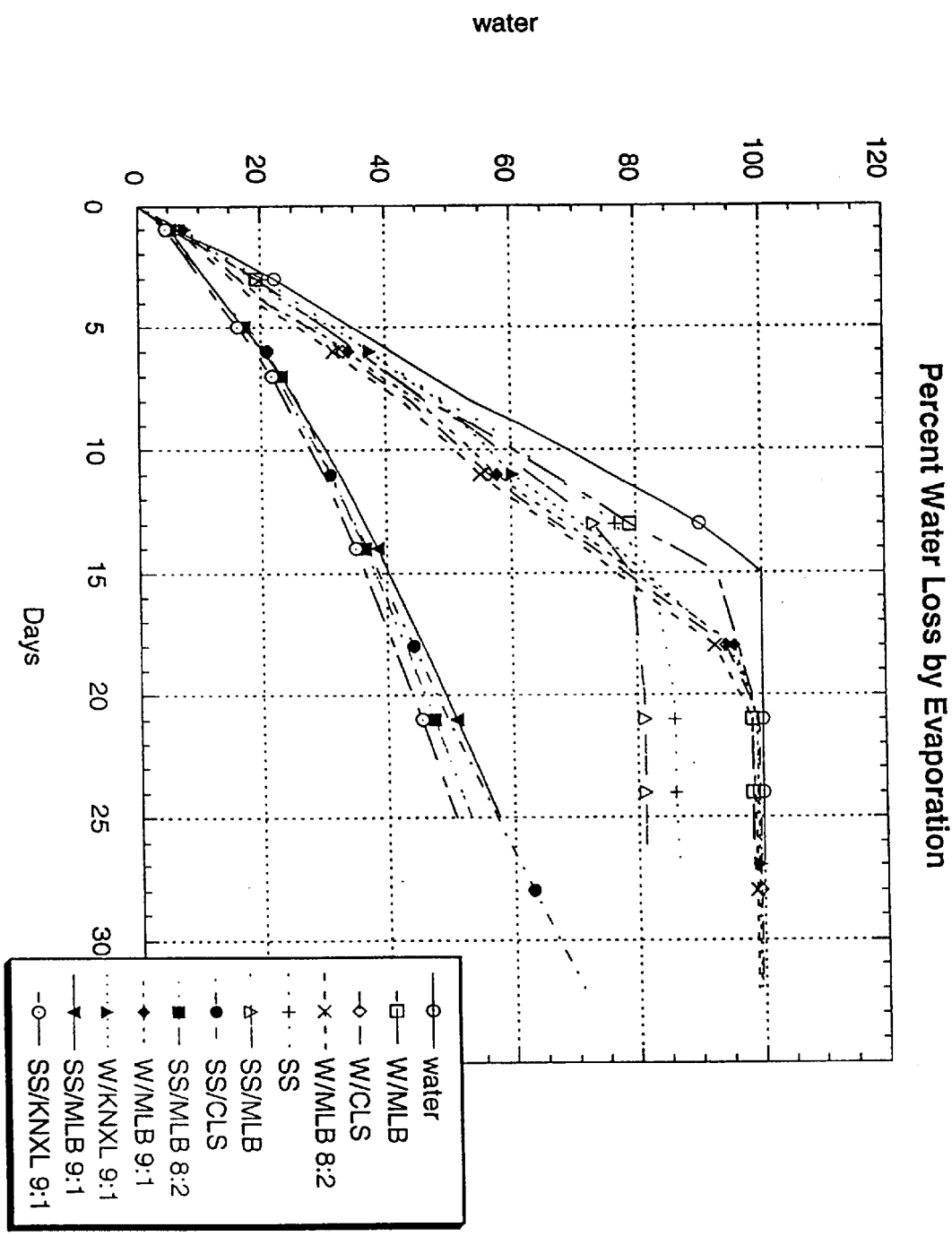
FIG. 1 illustrates the rate of water loss by evaporation from various solutions

As used herein, the term "low molecular weight compound" refers to a non-polymeric compound having a molecular weight less than about 600. The term "low molecular weight carbohydrate polymer" refers to a carbohydrate polymer having an average molecular weight below about 10,000 Mw.

Polymers which, when crosslinked, may be used in the present invention as absorbent polymers include ionically charged carbohydrates. Examples of these include ionically charged derivatives of starch, cellulose, guar, konjac, and mixtures thereof. Xanthan gum, pectin and carrageenan are charged carbohydrates and therefore need not be derivatized before being crosslinked. Other classes of polymers which may be used include polyacrylates, polyamides and starch-acrylonitrile copolymers. Of course, mixtures of the aforementioned polymers also may be used.

In most cases, hydrocolloid polymers are preferred over synthetic or part-synthetic polymers because hydrocolloid polymers are biodegradable. Preferably, the crosslinked absorbent polymer is a crosslinked ionically substituted derivative of starch such as crosslinked carboxymethyl starch.

The starch polymers of this invention may be obtained from, for example, potato starch, corn starch, wheat starch or tapioca starch. Examples of preferred starches are potato starch and corn starch.

The crosslinked absorbent polymers of this invention are substantially water-insoluble. Preferably the crosslinked polymers are at least 90% water insoluble, more preferably at least 95% water insoluble, and most preferably at least 99% water insoluble.

The crosslinked absorbent polymers of this invention may be prepared by reacting one or more of an ionically charged polymer with a crosslinking agent. Selection of a proper crosslinking agent will depend upon the polymer to be crosslinked. Alternatively, the crosslinked absorbent polymers may be prepared by crosslinking the polymer and then attaching an ionic substituent to the crosslinked polymer.

When the polymer to be crosslinked is starch or a derivative thereof, the crosslinking agent may be one which provides an ether bridge between polymer molecules. The ether bridge may have the formula —O—R—O— where R is an aliphatic group having 1–10 carbon atoms, which may be substituted by one or more hydroxyl groups. Preferably, R is —CH$_2$CH(OH)CH$_2$—, which is the case when the starch or derivative thereof is crosslinked using epichlorohydrin as the crosslinking agent.

In order to increase absorbency, cross-linked carbohydrate polymers should be substituted with ionic groups. The ionic groups, which are associated with mono-valent ions, may be attached to the polymer by ether linkages. Preferably, the ionic groups are of the formula Z—R$^1$— where R$^1$ is an alkylene group having 1 to 5 carbon atoms and Z is an anionic group such as, for example, carboxyl, sulphonyl, or phosphonyl or a cationic group of the formula

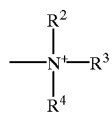

where R$^2$ is hydrogen or an alkyl group having 1 to 4 carbon atoms, and R$^3$ and R$^4$ are independently alkyl groups having 1 to 4 carbon atoms or are alkylene groups having 1 to 4 carbon atoms linked together to form a five or six membered heterocyclic ring. Particularly suitable materials are those wherein R$^1$ is an alkylene group containing 1 or 2 carbon atoms and Z is —CO$_2^-$. For example, preferred crosslinked absorbent polymers are crosslinked carboxymethylated starches. Typically, the degree of substitution of the ionic groups on the polymer will be between about 0.01 and about 2.0 per monomer. Preferably, the degree of substitution is at least 0.1, more preferably at least 0.2.

When Z is an anionic group, the counterion preferably is an alkali metal, alkaline earth metal, ammonium or substituted ammonium ion. The substituted ammonium derivatives may be those in which one or more hydrogen atoms are replaced by alkyl or hydroxy alkyl groups having one to four carbon atoms or in which the nitrogen atom forms part of a heterocyclic ring. For example, the substituted ammonium ion may be tetramethyl ammonium. When Z is an anionic group, preferred counterions are sodium, potassium and ammonium ions. When Z is a cationic group, the counterion may be, for example, chloride, bromide, phosphate or sulphate.

An etherifying agent may be used to link the ionic groups to the polymer via an ether linkage. These ionic groups may have the formula Z—R$^1$, where Z and R$^1$ are as described above. The etherifying agent may have the formula Z$^1$—R$^1$—X, where R$^1$ is an alkylene group of from 1 to 5 carbon atoms, Z$^1$ is an anionic or cationic group Z as defined above, or a group capable of being converted into such a charged group, and X is halogen or an epoxy group. Activated olefinic compounds carrying an ionic group or a group capable of being converted into a charged group also can be used. Preferably, R$^1$ is an alkylene group containing 1 or 2 carbon atoms and Z$^1$ is a carboxylic acid group or a salt thereof. Examples of etherifying agents are monochloroacetic acid, bromopropionic acid, chloroethylene sulphonic acid, chlorohydroxypropylene sulphonic acid, epoxypropylene sulphonic acid or 2-chloro-N,N-diethyl-ethylamine hydrochloride. Preferred etherifying agents are monochloroacetic acid and the sodium salt thereof.

When Z is an amine group, it may be quaternized prior to etherification of the polymer. For example, etherification may be conducted with the quaternary ammonium salt formed between epichlorohydrin and triethylamine. Examples of etherifying agents containing an activated olefinic group and a group capable of being converted into a charged group, e.g., with alkali, are acrylamide, acrylonitrile and ethylacrylate. Typically, the etherification is carried out in the presence of base. Sodium hydroxide is the preferred base, but other commonly known bases also may be used. The introduction of the charged groups increases the water retention value of the polymer.

Particularly preferred crosslinked absorbent polymers are the sodium and ammonium salts of carboxymethylated epichlorohydrin crosslinked starch.

The crosslinked absorbent polymers of this invention may be prepared by (i) treating the polymer with a crosslinking agent and (ii) attaching a charged (i.e. ionic) substituent to the crosslinked polymer. Alternatively, the steps may be reversed. That is, the polymer may be derivatized with an ionic group prior to crosslinking and then the derivatized polymer may be crosslinked. Derivitization of the polymer with the ionic substituent (e.g., reaction of the polymer with an etherifying agent) may be carried out before, during or after treatment of the polymer with the crosslinking agent.

In a preferred method of crosslinking the polymer, step (i) may be carried out by: (a) forming an aqueous alkaline slurry of the polymer and the crosslinking agent; and (b) rapidly heating the slurry by applying the slurry to a surface heated to between 100° C. and 180° C. to produce a crosslinked polymer in dried form.

Alternatively, step (i) may be carried out by: (a) forming an aqueous slurry of the polymer; (b) applying the slurry to a surface heated to between 100° C. and 180° C.; and (c) reacting the polymer with the crosslinking agent in the presence of water and base to produce a crosslinked polymer. In this procedure, the base may be included in the slurry.

Crosslinking agents that may be used in the present invention include, for example, epichlorohydrin, dichlorohydrin, dibromohydrin, 1,2–3,4-diepoxybutane, 1,2–7,8-diepoxyoctane, bis-epoxypropylether, 1,4-butanediol-bis-epoxypropylether and formaldehyde. Numerous other crosslinking agents that are well known by those skilled in the art also may be used. Preferably, the amount of crosslinking agent employed is that amount required to give a degree of substitution of the crosslinking groups within the range of 0.001 to 0.02. More preferably, the amount of crosslinking agent employed is that amount required to give a degree of substitution of the crosslinking groups within the range of 0.003 to 0.02. The function of the crosslinking agent is to insolubilize the polymer. However, crosslinking significantly beyond that required to insolubilize the polymer is not preferred because increasing amounts of the crosslinking agents give products having, for a given degree of ionic group substitution, lower water retention values.

In most instances, the crosslinking process will require the use of a base. One noteworthy exception is that when formaldehyde is employed as the crosslinking agent, acidic conditions are required. When alkaline conditions are required, sodium hydroxide, as well as a number of other bases, may be used. Since the degree of crosslinking necessary is small, the amount of base required to promote the crosslinking reaction also is small.

When a carboxylate salt is substituted onto the polymer, the substitution process preferably also comprises the additional steps of: (a) treating the polymer derivative with an acid to convert the carboxyl groups into their acid form; (b) washing the acid form of the polymer derivative with water to remove soluble salts; and (c) neutralizing the acid form of the polymer derivative with a base to reconvert the polymer derivative into an ionic form as an alkali metal, alkaline earth metal, ammonium or substituted ammonium salt. Preferably step (c) involves neutralizing the carboxylic acid form of the polymer derivative with excess ammonia followed by heating to dry the ammonium salt and remove excess ammonia.

The water retention value of the crosslinked absorbent polymers is dependent upon both the level of crosslinking and the level of ionic group substitution. Preferably, the level of substitution by the ionic groups is sufficient to provide the polymer with a water retention value of at least 6 grams of water per gram of polymer. More preferably, the crosslinked absorbent polymers of this invention have a water retention value of at least 12 g/g. Most preferably, the water retention value is between about 20 g/g and about 40 g/g.

The absorbent compositions of this invention may be prepared by combining a crosslinked absorbent polymer with a water-soluble low molecular weight compound. Water-soluble low molecular weight compounds which may be used in the compositions of this invention include, for example, carbohydrates such as sucrose, glucose, glycerin, ethylene glycol, sorbitol, fructose, maltodextrins, corn syrups, corn syrup solids and mixtures thereof. Generally, among low molecular weight non-polymeric carbohydrates, the solids tend to have a higher molecular weight than the liquids. Low molecular weight ionic compounds may be used, but they are generally disfavored because they may adversely affect the absorbent capacity of the polymer.

The selection of the water-soluble low molecular weight compound to be combined with the crosslinked polymer will depend upon the needs of the particular application. For example, where it is important that the absorbent composition be a solid, a solid low molecular weight compound will be used. On the other hand, where reducing the rate of evaporative moisture loss is determinative and the use of a liquid composition would be appropriate, a liquid low molecular weight compound (e.g., ethylene glycol) may be used. In the latter case, the use of a liquid low molecular weight compound may be preferred because liquid low molecular weight compounds typically are of lower molecular weight than solid low molecular weight compounds.

The absorbent compositions of this invention contain a crosslinked absorbent polymer and a water-soluble low molecular weight compound. The water-soluble low molecular weight compound should be present in an amount sufficient to reduce the rate of evaporation from the composition. Of course, this amount will vary depending upon the particular water-soluble low molecular weight compound employed. Preferably, the weight ratio of the crosslinked absorbent polymer to water-soluble low molecular weight compound is in a range of about 1:0.2 to about 1:30, more preferably about 1:2 to about 1:15.

These compositions may be prepared by any one of several methods. For example, when the water-soluble low molecular weight compound is a solid, it may be dry-blended with the crosslinked absorbent polymer. Alternatively, the compositions may be prepared by drying an absorbent polymer with the solid water-soluble low molecular weight compound. The solid low molecular weight compound may be dissolved in a solvent (e.g., water) and the resultant solution may be combined with the crosslinked polymer.

When the water-soluble low molecular weight compound is a liquid, it may be combined directly with the crosslinked absorbent polymer. Alternatively, the liquid low molecular weight compound may be dissolved in a solvent (e.g., water) and the resultant solution may be combined with the crosslinked polymer.

The compositions of this invention may also contain a low molecular weight carbohydrate polymer. The low molecular weight carbohydrate polymer may be used to replace a portion of the absorbent polymer without significantly affecting the absorbency of the composition. Preferably, the weight ratio of absorbent polymer to low molecular weight carbohydrate polymer is at least about 1.5:1, more preferably between about 2.0:1 and about 60:1, most preferably between about 4:1 and about 20:1.

Low molecular weight carbohydrate polymers which may be used in the present invention include low molecular weight hydrocolloids such as low molecular weight alginate, low molecular weight guar gum, low molecular weight carboxymethyl cellulose, low molecular weight carrageenan, low molecular weight xanthan gum, low molecular weight locust bean gum, low molecular weight pectin, and mixtures thereof.

When included in the composition, the low molecular weight carbohydrate polymer is preferably combined with the polymeric precursor of the absorbent polymer prior to crosslinking. For example, the absorbent polymer precursor may be combined with a solution containing a low molecular carbohydrate polymer, a crosslinking agent, and a base. This allows the low molecular weight carbohydrate polymer to be crosslinked with the absorbent polymer.

The crosslinking step may be followed by derivitization with a charged group. For example, the crosslinking step may be followed by (1) etherification under alkaline conditions; (2) treatment with acid for conversion of carboxylate groups to their acid form; (3) washing; and (4) neutralization. The resultant composition may be dried and milled using methods well known by those skilled in the art.

The following examples are intended to illustrate certain preferred embodiments of the invention, and no limitation of the invention is implied. All of the alginates used in the following experiments were obtained from The NutraSweet Kelco Company in San Diego, Calif.

COMPARATIVE EXAMPLE 1
Rate of Water Loss by Evaporation from Pure Water 50 grams of water were added to a 100 ml beaker and the beaker was placed in an oven at 30° C. for the duration of the experiment. The sample was weighed every day for 15 days and the percent water loss was calculated. The results of these measurements are set forth in Table 1.

COMPARATIVE EXAMPLE 2
Rate of Water Loss by Evaporation from a 0.5% Kelgin F Aqueous Solution (W/KNF)

In 100 ml beaker, 0.25 grams of Kelgin F were dissolved in 50 grams of water, and then the beaker was placed in an oven at 30° C. for the duration of the experiment. Kelgin F is a medium viscosity alginate. A 1% solution of Kelgin F has a viscosity of about 300 cP at 60 rpm measured with a Brookfield LV viscometer. The rate of water loss was determined as described in Comparative Example 1. The results of these measurements are set forth in Table 1.

COMPARATIVE EXAMPLE 3
Rate of Water Loss by Evaporation from a 0.5% Keltone HV Aqueous Solution (W/KTHV)

In 100 ml beaker, 0.25 grams of Keltone HV were dissolved in 50 grams of water, and then the beaker was placed in an oven at 30° C. for the duration of the experiment. Keltone HV is a medium viscosity alginate. A 1% solution of Keltone HV has a viscosity of about 400 cP at 60 rpm measured with a Brookfield LV viscometer. The rate of water loss was determined as described in Comparative Example 1. The results of these measurements are set forth in Table 1.

COMPARATIVE EXAMPLE 4
Rate of Water Loss by Evaporation from a 0.5% Kelcoloid O Aqueous Solution (W/KDO)

In 100 ml beaker, 0.25 grams of Kelcoloid O were dissolved in 50 grams of water, and then the beaker was placed in an oven at 30° C. for the duration of the experiment. Kelcoloid O is a propylene glycol alginate. A 1% solution of Kelcoloid O has a viscosity of about 25 cP at 60 rpm measured with a Brookfield LV viscometer. The rate of water loss was determined as described in Comparative Example 1. The results of these measurements are set forth in Table 1.

COMPARATIVE EXAMPLE 5
Rate of Water Loss by Evaporation from a Gel Having 0.5% Kelgin F, 0.8% Glucono-δ-lactone and 1.2% Dicalcium Phosphate Dehydrate (W/KNF Gel)

In a 100 ml beaker, 50 grams of water were gelled with 0.25 grams of Kelgin F, 0.4 grams of Glucono-δ-lactone and 0.6 grams of dicalcium phosphate dihydrate. The resultant gel was placed in an oven at 30° C. for the duration of the experiment. The rate of water loss was determined as described in Comparative Example 1. The results of these measurements are set forth in Table 1.

COMPARATIVE EXAMPLE 6
Rate of Water Loss by Evaporation from a Gel Having 0.5% Keltone HV, 0.8% Glucono-δ-lactone and 1.2% Dicalcium Phosphate Dihydrate (W/KTHV Gel)

In a 100 ml beaker, 50 grams of water were gelled with 0.25 grams of Keltone HV, 0.4 grams of glucono-delta-lactone and 0.6 grams of dicalcium phosphate dihydrate. The resultant gel was placed in an oven at 30° C. for the duration of the experiment. The rate of water loss was determined as described in Comparative Example 1. The results of these measurements are set forth in Table 1.

COMPARATIVE EXAMPLE 7
Rate of Water Loss by Evaporation from a 33% Sucrose Solution (SS)

In a 100 ml beaker, 25 grams of sucrose were dissolved in 50 grams of water, and the beaker was placed in an oven at 30° C. for the duration of the experiment. The rate of water loss by evaporation was determined as described in Comparative Example 1. The results of these measurements are set forth in Table 1.

COMPARATIVE EXAMPLE 8
Rate of Water Loss by Evaporation from an Aqueous Solution Having Kelgin F and 33% Sucrose (SS/KNF)

In a 100 ml beaker, 0.25 grams of Kelgin F and 25 grams of sucrose were dissolved in 50 grams of water, and the resultant solution was placed in an oven at 30° C. for the duration of the experiment. The rate of water loss was determined as described in Comparative Example 1. The results of these measurements are set forth in Table 1.

COMPARATIVE EXAMPLE 9
Rate of Water Loss by Evaporation from an Aqueous Solution Having Keltone HV and 33% Sucrose (SS/KTHV)

In a 100 ml beaker, 0.25 grams of Keltone HV and 25 grams of sucrose were dissolved in 50 grams of water, and the resultant solution was placed in an oven at 30° C. for the duration of the experiment. The rate of water loss was determined as described in Comparative Example 1. The results of these measurements are set forth in Table 1.

COMPARATIVE EXAMPLE 10
Rate of Water Loss by Evaporation from an Aqueous Solution Having Kelcoloid O and 33% Sucrose (SS/KDO)

In a 100 ml beaker, 0.25 grams of Kelcoloid O and 25 grams of sucrose were dissolved in 50 grams of water, and the resultant solution was placed in an oven at 30° C. for the duration of the experiment. The rate of water loss was determined as described in Comparative Example 1. The results of these measurements are set forth in Table 1.

COMPARATIVE EXAMPLE 11
Rate of Water Loss by Evaporation from a Gel Having 33% Sucrose, 0.5% Kelgin F, 0.8% Gucono-δ-lactone, and 1.2% Dicalcium Phosphate Dihydrate (SS/KNF Gel)

In a 100 ml beaker, 25 grams of sucrose were dissolved in 50 grams of water, and the resultant sucrose solution was gelled with 0.25 grams of Kelgin F, 0.4 grams of glucono-δ-lactone and 0.6 grams of dicalcium phosphate dihydrate. The resultant gel was placed in an oven at 30° C. for the duration of the experiment. The rate of water loss was determined as described in Comparative Example 1. The results of these measurements are set forth in Table 1.

COMPARATIVE EXAMPLE 12
Rate of Water Loss by Evaporation from Gel Having 33% Sucrose and 0.5% Keltone HV (SS/KTHV Gel)

In a 100 ml beaker, 25 grams of sucrose were dissolved in 50 grams of water, and the resultant sucrose solution was gelled with 0.25 grams of Keltone HV, 0.4 grams of glucono-δ-lactone and 0.6 grams of dicalcium phosphate dihydrate. The resultant gel was placed in an oven at 30° C. for the duration of the experiment. The rate of water loss was determined as described in Comparative Example 1. The results of these measurements are set forth in Table 1.

The results of Comparative Examples 1–12, summarized in Table 1, show the following: (a) the rate at which water evaporates is not influenced by the presence of dissolved polymers (compare Example 1 to Examples 2–6); (b) dissolution of a low molecular weight solute (e.g., sucrose) in water reduces the rate at which moisture is lost by evaporation (compare Example 1 to Example 7); (c) inclusion of a dissolved polymer (e.g., alginates) in a sucrose solution further reduces the rate at which moisture is lost (compare Example 1 to Example 7 and Examples 8, 9, and 10); and (d) gelation of the polymer dissolved in the sucrose solution brings about a slight further reduction in the rate at which moisture is lost (compare Example 7 to Examples 8, 9, and 10 and also to Examples 11, and 12, at day 7).

COMPARATIVE EXAMPLE 13
Rate of Water Loss by Evaporation from Pure Water 100 grams of water were added to a 250 ml beaker and the beaker was placed in an oven at 30° C. for the duration of the experiment. The sample was weighed at selected intervals and the percent water loss was calculated. The results of these measurements are set forth in FIG. 1 and Table 2.

COMPARATIVE EXAMPLE 14
Rate of Water Loss by Evaporation from Crosslinked Carboxymethyl Starch (W/CLS)

A crosslinked starch control was prepared in accordance with methods described in U.K. Patent No. 1,576,475, the entire contents of which are incorporated by reference herein. 1,000 grams of potato starch were slurried in 950 grams of water containing 8.4 mls of epichlorohydrin. To this slurry were added 5 grams of sodium hydroxide in 50 mls of water. The mixture was applied to a drum dryer to form a layer of about 0.5 mm in thickness. The roller was heated using steam at 40 psi. The crosslinked starch derivative was removed from the roller as a flake material and milled to 40 to 80 mesh. To 200 grams of the milled crosslinked potato starch were added 200 grams of a 34% aqueous sodium hydroxide solution followed by 100 grams of a 78% monochloroacetic acid aqueous solution. The mixture was allowed to stand overnight in a polyethylene bag.

The crosslinked starch derivative was dispersed in 10 times its weight of 1N hydrochloric acid, allowed to soak for 15 minutes, and then filtered. The gel cake was repeatedly dispersed in water and filtered, until the filtrate was substantially free of chloride ions. The water swollen washed cake was mixed with 200 ml of ammonium hydroxide (28 to 30% by weight) and the resultant mixture was allowed to stand overnight in a fume hood before drying in a forced air oven at 70° C. The resultant dry crosslinked carboxymethyl starch was milled to 40 to 80 mesh.

The rate of moisture loss by evaporation from 100 g of water containing 3.5 grams of the crosslinked carboxymethyl starch was determined using the procedures described in Comparative Example 13. The amount of crosslinked carboxymethyl starch added was the minimum amount required to absorb all of the water and provide a dry appearance to the swollen hydrogel (i.e., to eliminate the presence of excess water at the surface, at which water evaporation occurs). The results of these measurements are set forth in FIG. 1 and Table 2.

EXAMPLE 1
Rate of Water Loss from a Sucrose Solution Containing Crosslinked Carboxymethyl Starch (SS/CLS)

The rate of water loss by evaporation from a solution containing 100 grams of water, 5.8 grams of the crosslinked carboxymethyl starch of Comparative Example 14 and 50 grams of sucrose was determined as described in Comparative Example 13. The amount of crosslinked carboxymethyl starch added, was the minimum amount required to absorb all of the solution and provide a dry appearance to the swollen hydrogel (i.e., to eliminate the presence of excess solution at the surface, at which water evaporation occurs). The results of these measurements are set forth in FIG. 1 and Table 2.

COMPARATIVE EXAMPLE 15
Rate of Water Loss by Evaporation from a Crosslinked Carboxymethyl Starch/alginate (Manucol LB) 8:2 mixture (W/MLB 8:2)

A crosslinked carboxymethyl starch/alginate (Manucol LB) mixture was prepared in accordance with the methods described in Comparative Example 14 except that 800 grams of potato starch were slurried in 1,100 grams of water containing 200 grams of alginate (Manucol LB), and 8.4 mls of epichlorohydrin. To this slurry were added 5 grams of sodium hydroxide in 50 mls of water.

The rate of moisture loss by evaporation from 100 grams of water containing 7.1 grams of the crosslinked starch/alginate mixture was determined using procedures as described in Comparative Example 13. The amount of the mixture added was the minimum amount required to absorb all of the water and provide a dry appearance to the swollen hydrogel (i.e., to eliminate the presence of excess water at the surface, at which water evaporation occurs). The results of these measurements are set forth in FIG. 1 and Table 2.

EXAMPLE 2
Rate of Water Loss by Evaporation from a Sucrose Solution Containing a Crosslinked Carboxymethyl Starch/alginate (Manucol LB) 8:2 Mixture (SS/MLB 8:2)

The rate of water loss by evaporation from a solution containing 100 grams of water, 9.6 grams of the mixture of Comparative Example 15 and 50 grams of sucrose was determined as described in Comparative Example 13. The amount of the mixture added was the minimum amount required to absorb all of the solution and provide a dry appearance to the swollen hydrogel (i.e., to eliminate the presence of excess solution at the surface, at which water evaporation occurs). The results of these measurements are set forth in FIG. 1 and Table 2.

COMPARATIVE EXAMPLE 16
Rate of Water Loss by Evaporation from a Crosslinked Carboxymethyl Starch/alginate (Manucol LB) 9:1 Mixture (W/MLB 9:1)

A crosslinked carboxymethyl starch/alginate (Manucol LB) mixture was prepared as described in Comparative Example 15 except that 900 grams of potato starch were slurried in 1,100 grams of water containing 100 grams of alginate (Manucol LB), and 8.4 mls of epichlorohydrin. To this slurry were added 5 grams of sodium hydroxide in 50 mls of water.

The rate of moisture loss by evaporation from 100 grams of water containing 6.1 grams of the starch/alginate mixture was determined using procedures as described in Comparative Example 13. The amount of the mixture added was the minimum amount required to absorb all of the water and provide a dry appearance to the swollen hydrogel (i.e., to eliminate the presence of excess water at the surface, at which water evaporation occurs). The results of these measurements are set forth in FIG. 1 and Table 2.

EXAMPLE 3
Rate of Water Loss by Evaporation from a Sucrose Solution Containing a Crosslinked Carboxymethyl Starch/alginate (Manucol LB) 9:1 Mixture (SS/MLB 9:1)

The rate of water loss by evaporation from a solution containing 100 grams of water, 8.2 grams of the mixture of Comparative Example 16 and 50 grams of sucrose was determined as described in Comparative Example 13. The amount of the mixture added was the minimum amount required to absorb all of the solution and provide a dry appearance to the swollen hydrogel (i.e., to eliminate the presence of excess solution at the surface, at which water evaporation occurs). The results of these measurements are set forth in FIG. 1 and Table 2.

COMPARATIVE EXAMPLE 17
Rate of Water Loss by Evaporation from a Crosslinked Carboxymethyl Starch/alginate (Kelgin XL) 9:1 Mixture (w/KNXL 9:1)

A crosslinked carboxymethyl starch/alginate mixture was prepared as described in Comparative Example 15 except that 900 grams of potato starch were slurried in 1,100 grams of water containing 100 grams of alginate (Kelgin XL) and 8.4 mls of epichlorohydrin. To this slurry were added 5 grams of sodium hydroxide in 50 mls of water.

The rate of moisture loss by evaporation from 100 grams of water containing 5.7 grams of the starch/alginate mixture was determined using procedures as described in Comparative Example 13. The amount of the mixture added was the minimum amount required to absorb all of the water and provide a dry appearance to the swollen hydrogel (i.e., to eliminate the presence of excess water at the surface, at which water evaporation occurs). The results of these measurements are set forth in FIG. 1 and Table 2.

EXAMPLE 4
Rate of Water Loss by Evaporation from a Sucrose Solution Containing a Crosslinked Carboxymethyl Starch/alginate (Kelgin XL) 9:1 Mixture (SS/KNXL 9:1)

The rate of water loss by evaporation from a solution containing 100 grams of water, 7.7 grams of the mixture of Comparative Example 17 and 50 grams of sucrose was determined as described in Comparative Example 13. The amount of the mixture added was the minimum amount required to absorb all of the solution and provide a dry appearance to the swollen hydrogel (i.e., to eliminate the presence of excess solution at the surface, at which water evaporation occurs). The results of these measurements are set forth in FIG. 1 and Table 2.

COMPARATIVE EXAMPLE 18
Rate of Water Loss by Evaporation from an Aqueous Solution Containing Alginate (Manucol LB) (W/MLB)

In a 250 ml beaker, 0.5 grams of Manucol LB were dissolved in 100 grams of water, and the beaker was placed in an oven at 30° C. for the duration of the experiment. The rate of water loss by evaporation was determined as described in Comparative Example 13. The results of these measurements are set forth in FIG. 1 and Table 2.

COMPARATIVE EXAMPLE 19
Rate of Water Loss by Evaporation from a 33% Sucrose Solution (SS)

In a 250 ml beaker, 50 grams of sucrose were dissolved in 100 grams of water, and the beaker was placed in an oven at 30° C. for the duration of the experiment. The rate of water loss by evaporation was determined as described in Comparative Example 13. The results of these measurements are set forth in FIG. 1 and Table 2.

COMPARATIVE EXAMPLE 20
Rate of Water Loss by Evaporation from a Solution Containing Sucrose and Alginate (Manucol LB) (SS/MLB)

In a 250 ml beaker, 0.50 grams of Manucol LB and 50 grams of sucrose were dissolved in 100 grams of water, and the resultant solution was placed in an oven at 30° C. for the duration of the experiment. The rate of water loss was determined as described in Comparative Example 13. The results of these measurements are set forth in FIG. 1 and Table 2.

The results of Comparative Examples 13–20 and Examples 1–4, summarized in Table 2 and FIG. 1, support the trends seen in Table 1. Specifically, MLB, an ultra low viscosity alginate with a viscosity of around 4cps as measured on a Brookfield LV at 60 rpm, slightly reduces the rate of evaporative moisture loss when it is dissolved in both water and sucrose solution. The results in Table 2 and FIG. 1 also show the effect of superabsorbents on the rate of evaporative moisture loss. When added to water in sufficient amounts to absorb all of it, superabsorbents, exemplified by CLS, MLB 8:2, MLB 9:1, and KNXL 9:1, slightly reduce the rate of evaporative moisture loss (see W/CLS; W/MLB 8:2; W/MLB 9:1; W/KNXL 9:1). However, when used in the manner taught in this invention, namely by combining them with a low molecular weight solute, exemplified in these cases by sucrose, the rate of evaporative moisture loss is dramatically reduced (see SS/CLS; SS/MLB 8:2; SS/MLB 9:1; SS/KNXL 9:1).

TABLE 1

Percent Water Loss by Evaporation

| Days | Compar. Ex. 1 Water | Compar. Ex. 2 W/KNF | Compar. Ex. 3 W/KTHV | Compar. Ex. 4 W/KDO | Compar. Ex. 5 W/KNFGEL | Compar. Ex. 6 W/KTHVGEL | Compar. Ex. 7 SS | Compar. Ex. 8 SS/KNF | Compar. Ex. 9 SS/KTHV | Compar. Ex. 10 SS/KDO | Compar. Ex. 11 SS/KNFGEL | Compar. Ex. 12 SS/KTHVGEL |
|---|---|---|---|---|---|---|---|---|---|---|---|---|
| 0 | 0.00 | 0.00 | 0.00 | 0.00 | 0.00 | 0.00 | 0.00 | 0.00 | 0.00 | 0.00 | 0.00 | 0.00 |
| 1 | 10.0 | 9.40 | 9.20 | 9.60 | 9.80 | 9.60 | 9.00 | 7.80 | 8.00 | 8.80 | 7.80 | 8.40 |
| 2 | 21.4 | 20.0 | 19.4 | 20.4 | 21.2 | 20.8 | 19.4 | 16.8 | 17.4 | 18.8 | 17.4 | 18.0 |
| 3 | 32.8 | 31.0 | 30.6 | 32.2 | 33.2 | 32.6 | 30.0 | 26.6 | 26.8 | 29.4 | 26.8 | 27.6 |
| 4 | 44.0 | 41.2 | 41.0 | 43.0 | 44.4 | 43.2 | 40.0 | 35.4 | 36.0 | 39.4 | 35.4 | 36.8 |
| 7 | 75.0 | 70.6 | 70.8 | 73.8 | 76.8 | 73.2 | 66.4 | 59.4 | 60.2 | 65.8 | 56.8 | 58.8 |

TABLE 1-continued

Percent Water Loss by Evaporation

| Days | Compar. Ex. 1 Water | Compar. Ex. 2 W/KNF | Compar. Ex. 3 W/KTHV | Compar. Ex. 4 W/KDO | Compar. Ex. 5 W/KNFGEL | Compar. Ex. 6 W/KTHVGEL | Compar. Ex. 7 SS | Compar. Ex. 8 SS/KNF | Compar. Ex. 9 SS/KTHV | Compar. Ex. 10 SS/KDO | Compar. Ex. 11 SS/KNFGEL | Compar. Ex. 12 SS/KTHVGEL |
|---|---|---|---|---|---|---|---|---|---|---|---|---|
| 8 | 85.8 | 81.2 | 81.2 | 84.4 | 88.0 | 83.4 | 74.2 | 64.2 | 67.6 | 73.2 | 62.8 | 64.8 |
| 9 | 96.0 | 90.8 | 90.6 | 93.8 | 100 | 92.8 | 79.8 | 66.4 | 72.6 | 77.4 | 67.6 | 69.6 |
| 10 | 100 | 99.0 | 99.0 | 99.2 | 100 | 97.8 | 83.0 | 67.4 | 75.8 | 79.4 | 72.4 | 74.6 |
| 11 | 100 | 99.2 | 99.0 | 99.2 | 100 | 99.4 | 84.6 | 67.8 | 77.0 | 80.6 | 76.4 | 78.8 |
| 15 | 100 | 99.2 | 99.0 | 99.2 | 100 | 100 | 86.6 | 69.6 | 77.4 | 81.2 | 86.0 | 86.4 |

TABLE 2

Percent Water Loss by Evaporation

| Days | Comparative Example 13 water | Comparative Example 14 w/CLS | Comparative Example 15 w/MLB 8:2 | Comparative Example 16 w/MLB 9:1 | Comparative Example 17 w/KNXL 9:1 | Comparative Example 18 w/MLB | Comparative Example 19 SS | Comparative Example 20 SS/MLB | Example 1 SS/CLS | Example 2 SS/MLB 8:2 | Example 3 SS/MLB 9:1 | Example 4 SS/KNXL 9:1 |
|---|---|---|---|---|---|---|---|---|---|---|---|---|
| 0 | 0.00 | 0.00 | 0.00 | 0.00 | 0.00 | 0.00 | 0.00 | 0.00 | 0.00 | 0.00 | 0.00 | 0.00 |
| 1 | 5.90 | 7.50 | 6.50 | 7.60 | 7.80 | 5.20 | 5.40 | 5.10 | 4.70 | 5.50 | 5.20 | 4.50 |
| 2 | 15.0 | | | | | 13.0 | 13.8 | 13.1 | | | | |
| 3 | 22.2 | | | | | 19.3 | 20.4 | 19.5 | | | | |
| 4 | | 21.0 | 19.7 | 21.3 | 24.2 | | | | 14.4 | 14.3 | 14.2 | 13.3 |
| 5 | | 27.7 | 26.0 | 28.0 | 31.6 | | | | 18.0 | 17.2 | 17.3 | 16.2 |
| 6 | | 33.2 | 31.6 | 34.0 | 37.5 | | | | 20.9 | 20.2 | 20.4 | 19.1 |
| 7 | | 38.2 | 36.9 | 39.3 | 42.8 | | | | 23.3 | 22.6 | 23.2 | 21.7 |
| 8 | 53.7 | 44.1 | 42.8 | 45.4 | 48.8 | 46.8 | 49.3 | 46.4 | 25.9 | | | |
| 9 | 61.8 | | | | | | 54.2 | 66.3 | 53.1 | | | |
| 11 | | 56.4 | 55.0 | 57.7 | 60.3 | | | | 30.9 | 31.1 | 32.6 | 29.9 |
| 12 | | 61.4 | 60.1 | 62.8 | 65.3 | | | | 32.8 | | | |
| 13 | 90.2 | 67.3 | 66.2 | 88.8 | 71.1 | 78.9 | 76.5 | 73.1 | 35.0 | | | |
| 14 | | 73.0 | 71.6 | 74.3 | 76.8 | | | | 36.9 | 36.5 | 38.6 | 35.0 |
| 15 | 100 | | | | | 93.0 | 82.6 | 79.1 | | | | |
| 18 | | 94.3 | 92.5 | 95.6 | 94.9 | | | | 44.2 | | | |
| 19 | | | | | | | | | | 44.4 | 47.6 | 42.5 |
| 20 | | | | | | 98.3 | 85.9 | 81.1 | | | | |
| 21 | 100 | 99.4 | 98.3 | 99.1 | 99.1 | 98.3 | 86.0 | 81.2 | 49.6 | 47.4 | 50.9 | 45.4 |
| 22 | | | | | | 98.3 | 86.1 | 81.2 | | | | |
| 24 | | | | | | 98.3 | 86.1 | 81.2 | | | | |
| 25 | | | | | | | | | | 53.0 | 57.6 | 50.7 |
| 26 | | 99.5 | 98.8 | 99.2 | 99.4 | | | | 59.1 | | | |
| 27 | | | | | | 98.3 | 86.6 | 81.2 | | | | |
| 28 | | 99.5 | 98.8 | 99.2 | 99.4 | | | | 82.9 | | | |
| 32 | | 99.5 | 98.8 | 99.3 | 99.4 | | | | 70.8 | | | |

Other variations and modifications of this invention will be obvious to those skilled in the art. This invention is not limited except as set forth in the following claims.

What is claimed is:

1. An absorbent composition consisting essentially of about 1 part by weight of a crosslinked absorbent polymer, between about 1.5 to 60 parts by weight of a low molecular weight carbohydrate polymer, and about 0.2 parts by weight to 30 parts by weight of a water soluble low molecular weight compound having a molecular weight less than about 600 wherein said crosslinked absorbent polymer is characterized by: a water retention value greater than about 6 grams of water per gram of polymer; being at least about 90% water insoluble; containing a crosslinking agent having crosslinking groups thereon sufficient to yield a degree of substitution within the range of 0.003 to 0.02; wherein said low molecular weight carbohydrate polymer is a low molecular weight hydrocolloid selected from the group consisting of low molecular weight algin, low molecular weight guar gum, low molecular weight carboxymethyl cellulose, low molecular weight carrageenan, low molecular weight xanthan gum, low molecular weight locust bean gum, low molecular weight pectin, derivatives thereof and mixtures thereof.

2. The composition of claim 1, wherein said low molecular weight carbohydrate polymer is a low molecular weight alginate.

3. The composition of claim 1 wherein said low molecular weight carbohydrate polymer is crosslinked with said crosslinked absorbent polymer.

4. The composition of claim 3, wherein said low molecular weight carbohydrate polymer is ionically substituted.

5. The composition of claim 4, wherein said ionically substituted low molecular weight carbohydrate polymer is a low molecular weight carboxymethyl-substituted carbohydrate polymer.

6. The composition of claim 5, wherein said low molecular weight carboxymethyl-substituted carbohydrate polymer is a carboxymethyl-substituted algin polymer.

7. A method for preparing an absorbent composition consisting essentially of combining about 1 part by weight of a crosslinked absorbent polymer, between about 1.5 to 60 parts by weight of a low molecular weight carbohydrate polymer, and about 0.2 parts to 30 parts by weight of a water soluble low molecular weight compound having a molecular weight less than about 600 wherein said crosslinked absorbent polymer is characterized by: a water retention value greater than about 6 grams of water per gram of polymer; being at least 90% water insoluble; containing a crosslinking agent having crosslinking groups thereon sufficient to yield a degree of substitution within the range of 0.003 to 0.02: wherein said low molecular weight carbohydrate polymer is a low molecular weight hydrocolloid selected from the group consisting of low molecular weight algin, low molecular weight guar gum, low molecular weight carboxmethyl cellulose, low molecular weight carrageenan, low molecular weight xanthan gum, low molecular weight locust bean gum, low molecular weight pectin, derivatives thereof and mixtures thereof.

8. The method of claim 7, wherein the weight ratio of said crosslinked absorbent polymer to said low molecular weight compound is in a range of about 1:2 to about 1:15.

9. The method of claim 7, wherein said crosslinked absorbent polymer is prepared by (i) attaching ionic groups to a polymer, and crosslinking said ionically-substituted polymer, or (ii) crosslinking a polymer, and attaching ionic groups to said crosslinked polymer.

10. The method of claim 7, wherein said water-soluble low molecular weight compound is selected from the group consisting of carbohydrates, dihydroxy alcohols, trihydroxy alcohols, polyhydric alcohols, and mixtures thereof.

11. The method of claim 7, wherein the amount of said water-soluble low molecular weight compound combined with said crosslinked absorbent polymer is sufficient to reduce the rate of evaporation from an aqueous mixture containing said composition.

12. The method of claim 7, wherein said low molecular weight carbohydrate polymer is a low molecular weight alginate.

13. The method of claim 7, wherein said low molecular weight carbohydrate polymer is crosslinked with said crosslinked absorbent polymer.

14. The method of claim 7, wherein said low molecular weight carbohydrate polymer is ionically substituted.

15. The method of claim 14, wherein said ionically substituted low molecular weight carbohydrate polymer is a low molecular weight carboxymethyl-substituted carbohydrate polymer.

16. The method of claim 15, wherein said low molecular weight carboemethyl-substituted carbohydrate polymer is a carboxymethyl-substituted algin polymer.

17. The method of claim 7, wherein said crosslinked absorbent polymer has a water retention value between about 20 and about 40 grams of water per gram of polymer.

18. The method of claim 17, wherein said crosslinked absorbent polymer is substituted with an ionic group.

19. The method of claim 18, wherein the degree of substitution of said ionic group on said crosslinked polymer is between about 0.01 and about 2.0 per monomer.

20. The method of claim 18, wherein said water-soluble low molecular weight compound is selected from the group consisting of ethylene glycol, glycerol, propylene glycol, sucrose, glucose, sorbitol, fructose, maltodextrins, corn syrups, corn syrup solids, and mixtures thereof.

21. The method of claim 18, wherein said ionic group is represented by the formula $Z-R^1-$ where $R^1$ is an alkylene group having 1 to 5 carbon atoms and Z is either an anionic group selected from the group consisting of carboxyl, sulphonyl, and phosphonyl or cationic group of the formula

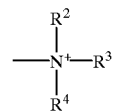

where $R^2$ is hydrogen or $C_{1-4}$ alkyl, and $R^3$ and $R^4$ are independently $C_{1-4}$ alkyl or alkylene groups linked together to form a five or six membered heterocyclic ring.

22. The method of claim 21, wherein said ionic group is $-CH_2CO_2$ or $-CH_2CH_2CO_2$.

23. The method of claim 18, wherein said tonically substituted crosslinked absorbent polymer is a derivative of a polymer selected from the group consisting of polyacrylates, polyamides, starch-polyacrylonitrile copolymers, starch, cellulose, xanthan gun, pectin, guar, carrageenan, konjac, and mixtures thereof.

24. The method of claim 23, wherein said ionically substituted crosslinked absorbent polymer is a derivative of starch.

25. The method of claim 24, wherein said ionically substituted crosslinked polymer is a carboxymethyl starch derivative.

* * * * *